(12) United States Patent
Litvak et al.

(10) Patent No.: US 9,776,000 B2
(45) Date of Patent: *Oct. 3, 2017

(54) PROGRAMMING SYSTEMS FOR ELICITING EVOKED RESPONSES IN A COCHLEAR IMPLANT PATIENT AND PERFORMING PREDETERMINED ACTIONS IN ACCORDANCE WITH THE EVOKED RESPONSES

(71) Applicant: ADVANCED BIONICS AG, Staefa (CH)

(72) Inventors: Leonid M. Litvak, Los Angeles, CA (US); Smita S. Agrawal, Stevenson Ranch, CA (US); Gulamali Emadi, Van Nuys, CA (US); Aniket Saoji, Newhall, CA (US); Charles C. Finley, Stevenson Ranch, CA (US); Guillermo A. Calle, Moorpark, CA (US); R. Tissa Karunasiri, Valencia, CA (US); Kanthaiah Koka, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/365,645

(22) Filed: Nov. 30, 2016

(65) Prior Publication Data

US 2017/0080227 A1    Mar. 23, 2017

(51) Int. Cl.
*A61N 1/36* (2006.01)
*A61B 5/04* (2006.01)
(Continued)

(52) U.S. Cl.
CPC ...... *A61N 1/36032* (2013.01); *A61B 5/04001* (2013.01); *A61B 5/121* (2013.01);
(Continued)

(58) Field of Classification Search
CPC .......................... A61B 5/04001; A61B 5/121
See application file for complete search history.

(56) References Cited

U.S. PATENT DOCUMENTS

| 5,776,179 A | 7/1998 | Ren et al. |
| 6,754,537 B1 | 6/2004 | Harrison et al. |

(Continued)

FOREIGN PATENT DOCUMENTS

| WO | WO-97/09863 | 3/1997 |
| WO | WO-2009/124165 | 10/2009 |

OTHER PUBLICATIONS

International Search Report and Written Opinion received in International Application No. PCT/US13/033607, dated May 31, 2013.

(Continued)

*Primary Examiner* — Carl H Layno
*Assistant Examiner* — Jennifer Ghand
(74) *Attorney, Agent, or Firm* — ALG Intellectual Property, LLC (57) ABSTRACT

An exemplary system includes 1) a programming device configured to be located external to a cochlear implant patient and communicatively coupled to a cochlear implant system associated with the patient, 2) a programming interface device communicatively coupled to the programming device and configured to be located external to the patient, and 3) a receiver communicatively coupled directly to the programming interface device. The programming device directs at least one of the cochlear implant system and the receiver to apply stimulation to the patient, records an evoked response that occurs in response to the stimulation, and performs a predetermined action in accordance with the evoked response. Corresponding systems and methods are also disclosed.

20 Claims, 9 Drawing Sheets

(51) Int. Cl.

| | | |
|---|---|---|
| *A61B 5/12* | (2006.01) | |
| *A61N 1/05* | (2006.01) | |
| *H04R 25/00* | (2006.01) | |
| *A61N 1/372* | (2006.01) | |
| *H04R 1/10* | (2006.01) | |

(52) U.S. Cl.
CPC ....... *A61N 1/0541* (2013.01); *A61N 1/37247* (2013.01); *H04R 1/1008* (2013.01); *H04R 25/00* (2013.01); *H04R 25/505* (2013.01); *H04R 25/554* (2013.01); *H04R 25/606* (2013.01); *H04R 25/70* (2013.01); *H04R 2225/67* (2013.01); *H04R 2460/03* (2013.01)

(56) References Cited

U.S. PATENT DOCUMENTS

| | | |
|---|---|---|
| 7,561,920 B2 | 7/2009 | Faltys et al. |
| 8,086,319 B2 | 12/2011 | van Dijk |
| 8,244,365 B2 | 8/2012 | Dijk et al. |
| 8,521,297 B2 | 8/2013 | Polak |
| 9,155,886 B2 | 10/2015 | James et al. |
| 2004/0152946 A1 | 8/2004 | Franck |
| 2005/0261748 A1 | 11/2005 | van Dijk |
| 2007/0135862 A1 | 6/2007 | Nicolai et al. |
| 2008/0249589 A1 | 10/2008 | Cornejo Cruz et al. |
| 2008/0319508 A1 | 12/2008 | Botros et al. |
| 2009/0240307 A1 | 9/2009 | Seligman |
| 2009/0254149 A1 | 10/2009 | Polak |
| 2009/0259140 A1 | 10/2009 | Buchman |
| 2010/0030012 A1 | 2/2010 | Meskens |
| 2010/0145411 A1 | 6/2010 | Spitzer |
| 2010/0198301 A1 | 8/2010 | Smith |
| 2011/0082521 A1 | 4/2011 | Botros et al. |

OTHER PUBLICATIONS

International Search Report and Written Opinion received in International Application No. PCT/US13/033605, dated Jul. 1, 2013.
International Search Report and Written Opinion received in International Application No. PCT/US13/033604, dated Jul. 1, 2013.
Miller, Charles A., et al., "Auditory Nerve Fiber Responses to Combined Acoustic and Electric Stimulation", *Journal of the Association for Research in Otolaryngology*, Springer-Verlag, NE, vol. 10, No. 3, Feb. 10, 2009, pp. 425-445.
Payton, Lin et al., "Ipsilateral Masking Between Acoustic and Electric Stimulations", *The Journal of the Acoustical Society of America, American Institute of Physics for the Acoustical Society of America*, New York, NY, US, vol. 130, No. 2, Aug. 1, 2011, pp. 858-865.
Davis, "An Active Process in Cochlear Mechanics", *Hearing Research*, 9 (1983) 79-90, Elsevier Biomedical Press.
Kohlloffel, "Longitudinal Amplitude and Phase Distribution of the Cochlear Microphonic (Guinea Pig) and Spatial Filtering", *J. Sound Vib.* (1970) 11 (3), 325-334.
Tasaki, et al., "The Space-Time Pattern of the Cochlear Microphonics (Guinea Pig), as Recorded by Differential Electrodes", *The Journal of the Acoustical Society of America*, vol. 24, No. 5, Sep. 1952.
Non-Final Office Action received in U.S. Appl. No. 14/386,735 dated Jul. 20, 2015.
Non-Final Office Action received in U.S. Appl. No. 14/386,331 dated Jul. 21, 2015.
Non-Final Office Action received in U.S. Appl. No. 14/386,330 dated Dec. 7, 2015.
Final Office Action received in U.S. Appl. No. 14/386,331 dated Jan. 20, 2016.
Final Office Action received in U.S. Appl. No. 14/386,735 dated Jan. 20, 2016.
Non-Final Office Action received in U.S. Appl. No. 14/386,331 dated Jun. 17, 2016.
Non-Final Office Action received in U.S. Appl. No. 14/386,735 dated Jun. 29, 2016.

PROGRAMMING SYSTEMS FOR ELICITING EVOKED RESPONSES IN A COCHLEAR IMPLANT PATIENT AND PERFORMING PREDETERMINED ACTIONS IN ACCORDANCE WITH THE EVOKED RESPONSES

RELATED APPLICATIONS

The present application is a continuation application of U.S. patent application Ser. No. 14/386,735, filed Sep. 19, 2014 and issued as U.S. Pat. No. 9,550,061, which application is a U.S. National Stage Entry of PCT Application No. PCT/US2013/033607, filed Mar. 22, 2013, which application claims the benefit of U.S. Provisional Patent Application No. 61/614,129, filed on Mar. 22, 2012, the contents of which are hereby incorporated by reference in their entirety.

BACKGROUND INFORMATION

The effectiveness of a cochlear implant system may be affected by a number of different factors. For example, surgical complications (e.g., a misalignment of an electrode array within the cochlea, destruction of hair cells during implantation of a cochlear implant, etc.) and post-surgery complications (e.g., residual hearing loss, wax buildup in the ear, infections, and component failure) may be detrimental to cochlear implant system performance. Unfortunately, many of these factors are not readily discernible, thereby making it difficult or impossible to account for them (e.g., by adjusting one or more control parameters governing an operation of the cochlear implant system). Hence, a patient may unknowingly suffer from sub-optimal cochlear implant system performance.

Moreover, some patients already fitted with a cochlear implant system may be candidates for an electro-acoustic stimulation ("EAS") system (i.e., a system that provides both electrical and acoustic stimulation). It would be desirable to objectively test whether a patient is a candidate for an EAS system before upgrading the patient's cochlear implant system to an EAS system.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Programming systems for eliciting evoked responses in a cochlear implant patient and performing predetermined actions in accordance with the evoked responses are described herein. As will be described below, an exemplary programming system includes 1) a programming device configured to be located external to a cochlear implant patient and communicatively coupled to a cochlear implant system associated with the patient, 2) a programming interface device communicatively coupled to the programming device and configured to be located external to the patient, and 3) a receiver communicatively coupled directly to the programming interface device. The programming device directs at least one of the cochlear implant system and the receiver (e.g., by communicating with the cochlear implant system and/or the receiver by way of the programming interface device) to apply stimulation to the patient, records an evoked response that occurs in response to the stimulation, and performs a predetermined action in accordance with the evoked response.

For example, during a consultation between a cochlear implant patient and a clinician, the clinician may connect a programming system to a cochlear implant system being used by the patient. This may be done in any suitable manner. For example, the clinician may connect (e.g., by way of a cable) a programming interface device (e.g., a clinician's programming interface ("CPI") device) to a sound processor included in the cochlear implant system. The programming interface device may also be connected (e.g., by way of one or more cables) to a programming device (e.g., a personal computer, a handheld device, a mobile computing device, etc.) and to a receiver configured to be in communication with an ear of the patient.

In this configuration, the clinician may provide input and/or otherwise initiate a programming session in which the programming device directs the cochlear implant system to apply electrical stimulation to the patient by way of one or more electrodes included in an electrode array implanted within a cochlea of the patient and/or the receiver to apply acoustic stimulation to the patient. The programming device may then record an evoked response that occurs in response to the electrical and/or acoustic stimulation and compare the evoked response to a baseline response and/or one or more previously recorded evoked responses. If the evoked response differs from the baseline response and/or the one or more previously recorded evoked responses (e.g., if the evoked response is not within a predetermined range of the baseline response and/or the one or more previously recorded evoked responses), the programming device may adjust one or more control parameters governing an operation of the cochlear implant system, notify the patient and/or another user of the potentially problematic evoked response, and/or take any other suitable action as may serve a particular implementation. These and other examples will be described in more detail below.

By eliciting an evoked response and then performing one or more predetermined actions in accordance with the evoked response, the systems and methods described herein may facilitate optimal performance of a cochlear implant system, assist in evaluating one or more conditions (e.g., a residual hearing status) of the patient, determine whether the patient is a candidate for an EAS system, and/or otherwise provide benefit to the patient.

As used herein, an "evoked response" may include any type of cochlear response and/or neural response. Exemplary cochlear responses include, but are not limited to, cochlear microphonics, summating potentials, otoacoustic emissions, etc. Exemplary neural responses include, but are not limited to, auditory nerve responses, brainstem responses, compound action potentials, frequency following responses, etc. An evoked response may additionally or alternatively include a stapedius response and/or any other type of response that may occur in response to application of electrical and/or acoustic stimulation.

Additional or alternative manners in which an evoked response may be elicited are described in more detail in PCT Application No. PCT/US2013/033605, which is incorporated herein by reference in its entirety.

Figure 1:
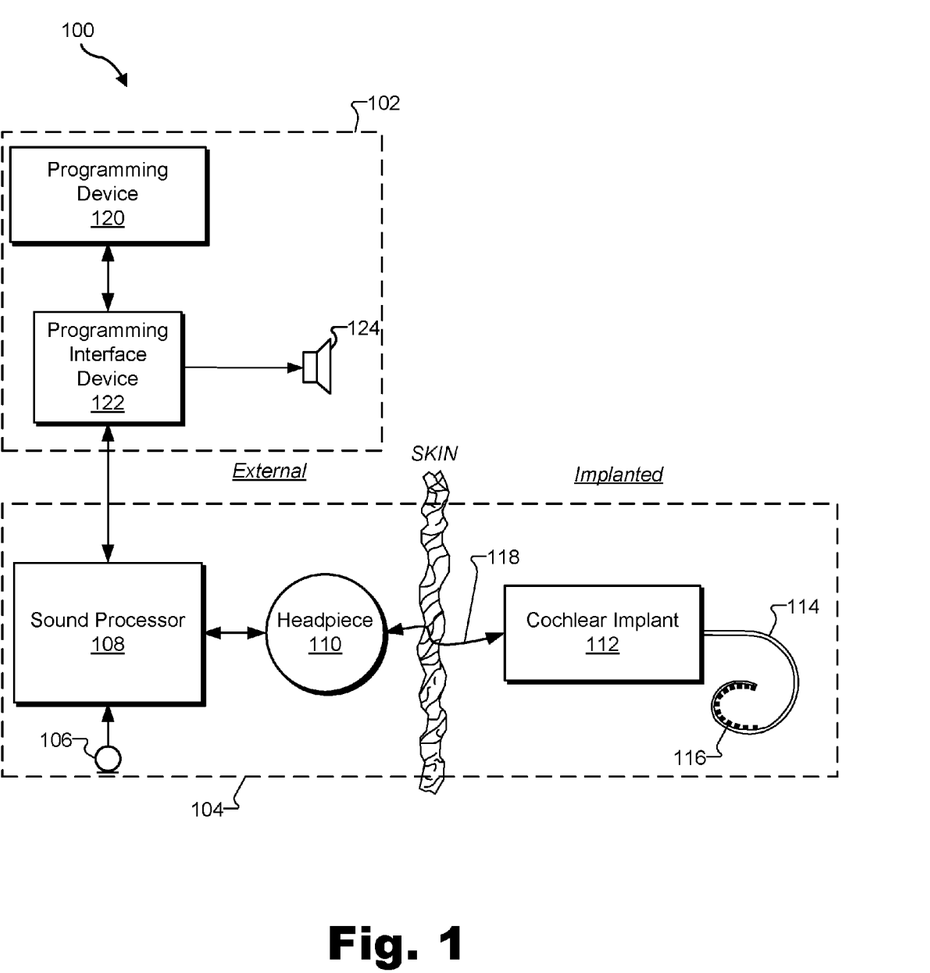
FIG. 1 illustrates an exemplary configuration in which a programming system is communicatively coupled to a cochlear implant system according to principles described herein.

FIG. 1 illustrates an exemplary configuration 100 in which a programming system 102 is communicatively coupled to a cochlear implant system 104. Programming system 102 and cochlear implant system 104 may be communicatively coupled in any suitable manner, including in any of the manners described herein.

As shown, cochlear implant system 104 may include a microphone 106, a sound processor 108, a headpiece 110 having a coil disposed therein, a cochlear implant 112, and an electrode array 114 with a plurality of electrodes 116 disposed thereon. Additional or alternative components may be included within cochlear implant system 104 as may serve a particular implementation.

As shown, various components of cochlear implant system 104 may be located external to the patient including, but not limited to, microphone 106, sound processor 108 and headpiece 110. Various components of cochlear implant system 104 may be implanted within the patient including, but not limited to, cochlear implant 112 and electrode array 114. Additional or alternative components may be included within cochlear implant system 104 as may serve a particular implementation.

Microphone 106 may be configured to detect audio signals (i.e., audio content) presented to the patient. Microphone 106 may be implemented in any suitable manner. For example, microphone 106 may include a "T-Mic" or the like that is configured to be placed within the concha of the ear near the entrance to the ear canal. Such a microphone may be held within the concha of the ear near the entrance of the ear canal by a boom or stalk that is attached to an ear hook configured to be selectively attached to sound processor 108. Additionally or alternatively, microphone 106 may be implemented by one or more microphones disposed within headpiece 110, one or more microphones disposed within sound processor 108, and/or any other suitable microphone as may serve a particular implementation.

Sound processor 108 (i.e., one or more components included within sound processor 108) may be configured to direct cochlear implant 112 to generate and apply electrical stimulation (also referred to herein as "stimulation current") representative of one or more audio signals (e.g., one or more audio signals detected by microphone 106, input by way of an auxiliary audio input port, etc.) to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. To this end, sound processor 108 may process the one or more audio signals in accordance with a selected sound processing strategy or program to generate appropriate stimulation parameters for controlling cochlear implant 112. Sound processor 108 may include or be implemented by a behind-the-ear ("BTE") unit, a body worn device, and/or any other sound processing unit as may serve a particular implementation.

In some examples, sound processor 108 may wirelessly transmit stimulation parameters (e.g., in the form of data words included in a forward telemetry sequence) and/or power signals to cochlear implant 112 by way of a wireless communication link 118 between headpiece 110 and cochlear implant 112. It will be understood that communication link 118 may include a bi-directional communication link and/or one or more dedicated uni-directional communication links.

Headpiece 110 may be communicatively coupled to sound processor 108 and may include an external antenna (e.g., a coil and/or one or more wireless communication components) configured to facilitate selective wireless coupling of sound processor 108 to cochlear implant 112. Headpiece 110 may additionally or alternatively be used to selectively and wirelessly couple any other external device to cochlear implant 112. To this end, headpiece 110 may be configured to be affixed to the patient's head and positioned such that the external antenna housed within headpiece 110 is communicatively coupled to a corresponding implantable antenna (which may also be implemented by a coil and/or one or more wireless communication components) included within or otherwise associated with cochlear implant 112. In this manner, stimulation parameters and/or power signals may be wirelessly transmitted between sound processor 108 and cochlear implant 112 via a communication link 118 (which may include a bi-directional communication link and/or one or more dedicated uni-directional communication links as may serve a particular implementation).

Cochlear implant 112 may include any type of implantable stimulator that may be used in association with the systems and methods described herein. For example, cochlear implant 112 may be implemented by an implantable cochlear stimulator. In some alternative implementations, cochlear implant 112 may include a brainstem implant and/or any other type of implant that may be implanted within a patient and configured to apply stimulation to one or more stimulation sites located along an auditory pathway of a patient.

In some examples, cochlear implant 112 may be configured to generate electrical stimulation representative of an audio signal processed by sound processor 108 (e.g., an audio signal detected by microphone 106) in accordance with one or more stimulation parameters transmitted thereto by sound processor 108. To this end, cochlear implant 112 may include one or more current generators. In some examples, cochlear implant 112 may include one or more lock-in amplifiers. A lock-in amplifier allows for a relatively high signal-to-noise ratio when the expected phase and waveform of the evoked response is known ahead of time.

Cochlear implant 112 may be further configured to apply the electrical stimulation to one or more stimulation sites within the patient via one or more electrodes 116 disposed along electrode array 114. In some examples, cochlear implant 112 may include a plurality of independent current sources each associated with a channel defined by one or more of electrodes 116. In this manner, different stimulation current levels may be applied to multiple stimulation sites simultaneously by way of multiple electrodes 116.

Figure 2:
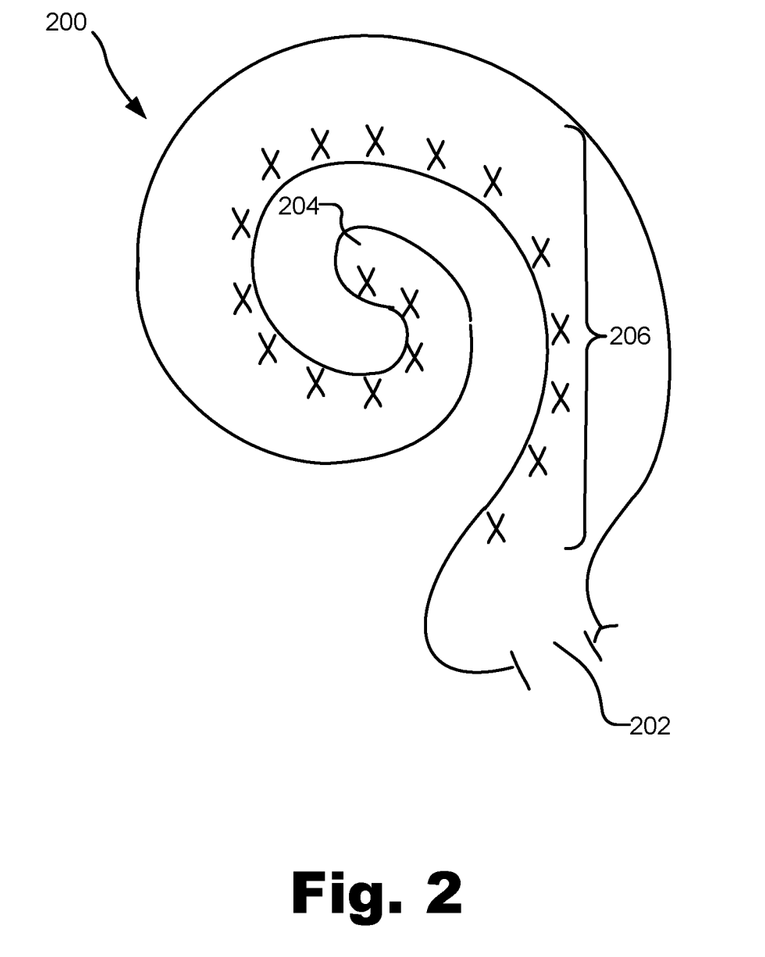
FIG. 2 illustrates a schematic structure of the human cochlea according to principles described herein.

FIG. 2 illustrates a schematic structure of the human cochlea 200 into which electrode array 114 may be inserted. As shown in FIG. 2, the cochlea 200 is in the shape of a spiral beginning at a base 202 and ending at an apex 204. Within the cochlea 200 resides auditory nerve tissue 206, which is denoted by Xs in FIG. 2. The auditory nerve tissue 206 is organized within the cochlea 200 in a tonotopic manner. Relatively low frequencies are encoded at or near the apex 204 of the cochlea 200 (referred to as an "apical region") while relatively high frequencies are encoded at or near the base 202 (referred to as a "basal region"). Hence, electrical stimulation applied by way of electrodes disposed within the apical region (i.e., "apical electrodes") may result in the patient perceiving relatively low frequencies and electrical stimulation applied by way of electrodes disposed within the basal region (i.e., "basal electrodes") may result in the patient perceiving relatively high frequencies. The delineation between the apical and basal electrodes on a particular electrode lead may vary depending on the insertion depth of the lead, the anatomy of the patient's cochlea, and/or any other factor as may serve a particular implementation.

Returning to FIG. 1, programming system 102 may include various components configured to be located external to the patient. As shown, programming system 102 may include a programming device 120, a programming interface device 122, and a receiver 124 (also referred to as a "loudspeaker"). Programming system 102 may include additional or alternative components, as will be described below.

Programming device 120 may be implemented by any suitable combination of computing devices including, but not limited to, a fitting station, a personal computer, a laptop computer, a handheld device, a mobile device (e.g., a mobile phone), and/or any other suitable component as may serve a particular implementation. In some examples, programming device 120 may provide one or more graphical user interfaces ("GUIs") (e.g., by presenting the one or more GUIs by way of a display screen) with which a clinician or other user may interact.

As will be described below, programming device 120 may direct cochlear implant device 104 and/or receiver 124 to apply stimulation to a patient, record an evoked response that occurs in response to the stimulation, and perform one or more predetermined actions in accordance with the evoked response. Exemplary predetermined actions that may be performed by programming device 120 will be described below.

Programming interface device 122 may include any combination of devices configured to facilitate communication between programming device 120 and one or more other systems and/or components. For example, programming interface device 122 may facilitate communication between programming device 120 and cochlear implant system 104, between programming device 120 and receiver 124, and/or between programming device 120 and any other device or component as may serve a particular implementation.

In some examples, programming interface device 122 may be implemented by a clinician's programming interface ("CPI") device that includes one or more ports configured to facilitate selective and direct connection (e.g., by way of one or more wired cables) to any of the components described herein. For example, programming interface device 122 may be selectively and directly connected to programming device 120, sound processor 108 of cochlear implant system 104, and/or receiver 124. Additionally or alternatively, programming interface device 122 may facilitate wireless communication between any of the components described herein.

As shown in FIG. 1, programming interface device 122 may be a standalone device (i.e., separate from programming device 120). Alternatively, programming interface device 122 may be integrated into programming device 120.

Receiver 124 may be communicatively coupled directly to programming interface device 122 and may be configured to be in communication with an ear of the patient. For example, receiver 124 may be integrated into an earmold configured to be located within the outer ear of the patient. The earmold may include any type of earmold that may be at least partially disposed within the outer ear of the patient. For example, the earmold may include an open dome configured to allow the ear to remain partially open (e.g., an open dome tip made from a soft silicone material and configured to resemble a tulip or flower bud), a closed dome configured to entirely close off the ear canal, a foam dome, and/or any other type of dome as may serve a particular implementation. As will be described in more detail below, receiver 124 may be configured to apply acoustic stimulation to the patient as directed by programming device 120. As shown in FIG. 1, receiver 124 is separate from cochlear implant system 104 (i.e., not connected directly to sound processor 108).

Figure 3:
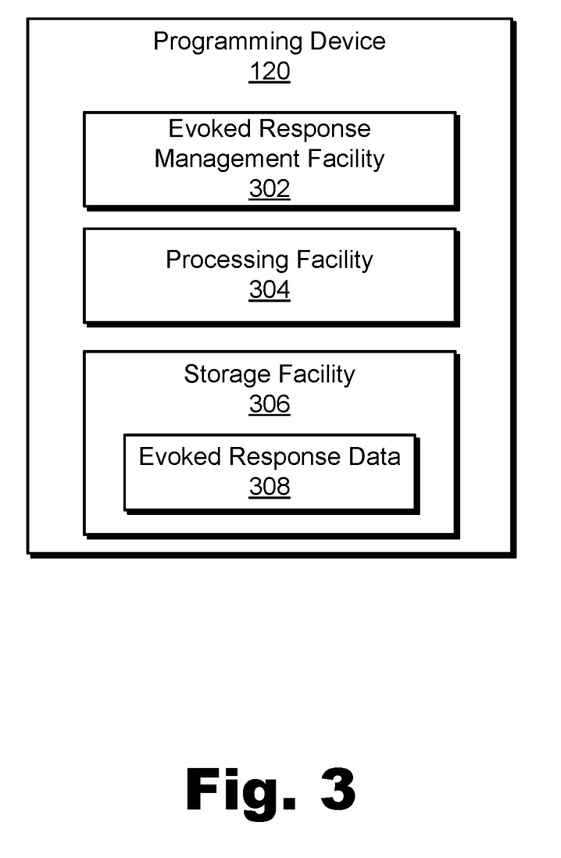
FIG. 3 illustrates exemplary components of a programming device according to principles described herein.

FIG. 3 illustrates exemplary components of programming device 120. As shown in FIG. 3, programming device 120 may include an evoked response management facility 302, a processing facility 304, and a storage facility 306, which may be in communication with one another using any suitable communication technologies. One or more of facilities 302-306 may include one or more computing devices and/or processors configured to perform one or more of the functions described herein. Facilities 302-306 will now be described in more detail.

Evoked response management facility 302 may be configured to perform one or more evoked response management operations. For example, evoked response management facility 302 may be configured to attempt to elicit an evoked response within a patient. This may be performed in any suitable manner. For example, evoked response management facility 302 may direct cochlear implant system 104 and/or receiver 124 to apply stimulation to the patient and then determine whether an evoked response occurs in response to the stimulation. The presence or absence of an evoked response may be indicative of one or more conditions (e.g., a residual hearing status of the patient, auditory neuropathy, etc.).

Evoked response management facility 302 may direct cochlear implant system 104 and/or receiver 124 (e.g., by way of programming interface device 122) to apply stimulation to the patient in any suitable manner. For example, evoked response management facility 302 may direct cochlear implant system 104 to apply electrical stimulation to the patient by way of at least one electrode 116 included in electrode array 114 (i.e., by transmitting one or more commands to sound processor 108 by way of programming interface device 122 for sound processor 108 to direct cochlear implant 112 to apply the electrical stimulation). The electrical stimulation may have any suitable characteristic. For example, the electrical stimulation may include monopolar stimulation. The electrode to which the electrical stimulation is applied may be any electrode located within the cochlea of the patient (e.g., the most apical electrode included in electrode array 114).

As another example, evoked response management facility 302 may direct receiver 124 to apply acoustic stimulation to the patient. The acoustic stimulation may have any suitable characteristic as may serve a particular implementation. For example, the acoustic stimulation may include a relatively low frequency tone burst (e.g., a 125 Hz tone burst).

As another example, evoked response management facility 302 may direct cochlear implant system 104 and receiver 124 to concurrently apply electrical stimulation and acoustic stimulation to the patient.

Evoked response management facility 302 may determine whether an evoked response occurs in response to the stimulation (i.e., the electrical and/or acoustic stimulation) in any suitable manner. For example, evoked response management facility 302 may use one or more electrodes to monitor for and record the evoked response. For example, a cochlear response (e.g., cochlear microphonics) may be recorded using one or more electrodes positioned within the cochlea (e.g., one or more of electrodes 116), one or more electrodes positioned within the round window, and/or one or more electrodes positioned at any other suitable location relatively near the cochlea. Likewise, a neural response (e.g., an auditory nerve response and/or a compound action potential) may be recorded using one or more electrodes positioned within or near the cochlea. It will be recognized that the electrode(s) used to record the evoked response may be disposed on a lead that has been inserted into the cochlea (e.g., electrode array 114), on a fly lead that has been positioned at any other suitable location within the patient, or on any other lead as may serve a particular implementation.

In some examples, one or more electrodes located external to the patient may be used to record an evoked response. For example, a brainstem response may be recorded using one or more non-invasive electrodes that have been affixed externally to the head of the patient.

In some examples, evoked response management facility 302 may use a microphone configured to be located within the ear canal of the patient to detect and record an evoked response (e.g., one or more otoacoustic emissions). These and other exemplary configurations that may be used to record evoked responses will be described in more detail below.

Evoked response management facility 302 may be configured to perform one or more predetermined actions in accordance with an evoked response that occurs in response to the stimulation (or in accordance with an evoked response not occurring in response to the stimulation). Exemplary predetermined actions that may be performed by evoked response management facility 302 will be described in more detail below.

Processing facility 304 may be configured to perform one or more processing operations. For example, processing facility 304 may perform one or more programming and/or fitting operations associated with cochlear implant system 104.

Storage facility 306 may be configured to maintain evoked response data 308 generated and/or utilized by evoked response management facility 302 and/or processing facility 304. In some examples, programming device 120 may store data representative of an evoked response within storage facility 306. Storage facility 306 may be configured to maintain additional or alternative data as may serve a particular implementation.

Various configurations that may be used to record various types of evoked responses will now be described. It will be recognized that the configurations described herein are merely illustrative of the various different configurations that may be used to record evoked responses in accordance with the systems and methods described herein.

Figure 4:
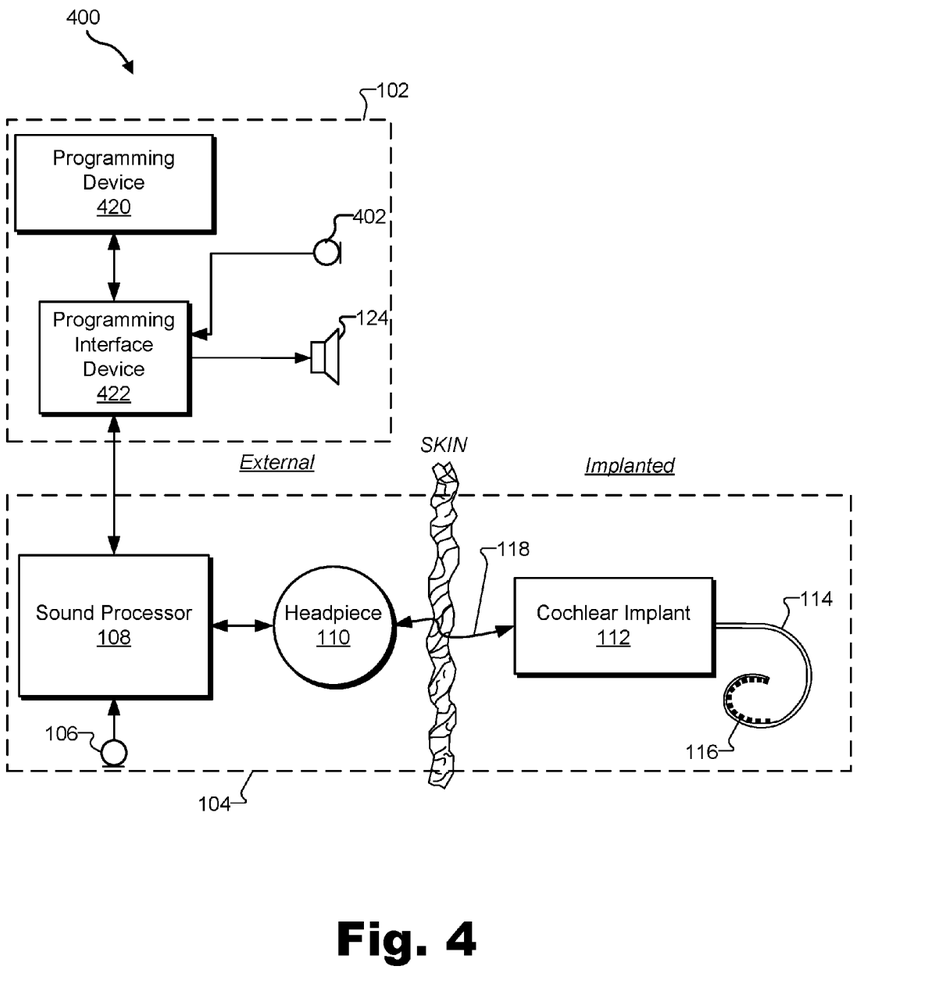
FIG. 4 illustrates an exemplary configuration that may be used to record an evoked response according to principles described herein.

FIG. 4 illustrates an exemplary configuration 400 that may be used to record an evoked response in accordance with the systems and methods described herein. Configuration 400 is similar to configuration 100, except that programming system 102 further includes a microphone 402 communicatively coupled to programming device 120. Microphone 402 may be configured to be located in an ear canal of the patient and may be used by programming device 120 to detect and record one or more otoacoustic emissions that occur in response to electrical and/or acoustic stimulation being applied to the patient. As used herein, "otoacoustic emissions" refer to sounds generated from within the inner ear in response to stimulation. In some examples, otoacoustic emissions may be indicative of inner ear health. For example, if programming device 120 does not detect a presence of otoacoustic emissions in response to stimulation, this may be indicative of a damaged or unhealthy inner ear.

Programming device 120 may additionally or alternatively use one or more electrodes 116 included in electrode array 114 to record one or more evoked responses. Exemplary evoked responses that may be recorded using an electrode disposed within the cochlea, such as one of electrodes 116, include, but are not limited to, neural responses and one or more types of cochlear responses.

Figure 5:
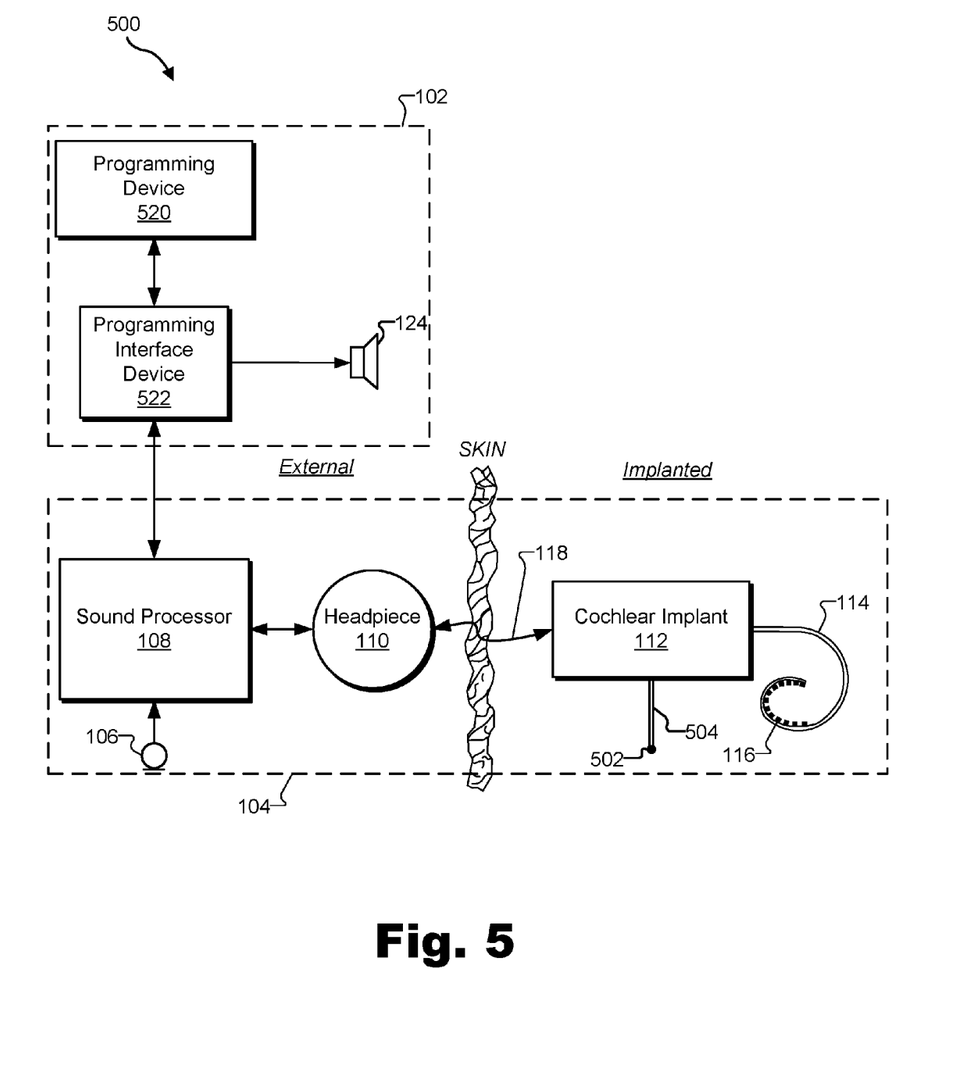
FIG. 5 illustrates another exemplary configuration that may be used to record an evoked response according to principles described herein.

FIG. 5 illustrates another exemplary configuration 500 that may be used to record an evoked response in accordance with the systems and methods described herein. Configuration 500 is similar to configuration 100, except that configuration 500 further includes an extra-cochlear electrode 502 communicatively coupled to cochlear implant 112. While FIG. 5 shows extra-cochlear electrode 502 communicatively coupled to cochlear implant 112, it will be recognized that extra-cochlear electrode 502 may alternatively be coupled to programming system 102 (e.g., to programming interface device 522).

Extra-cochlear electrode 502 may include any type of electrode not located within the cochlea. For example, extra-cochlear electrode 502 may include a ring electrode, an electrode configured to be positioned within the round window, a stapedius electrode configured to be in communication with the stapedius muscle (i.e., coupled to the stapedius muscle and/or the stapedius tendon), and/or any other suitable electrode. In some examples, extra-cochlear electrode 502 is disposed on a lead 504 communicatively coupled to cochlear implant system 104. Alternatively, extra-cochlear electrode 502 may be disposed on a portion of electrode array 114 that is not located within the cochlea.

In some examples, the use of an extra-cochlear electrode, such as extra-cochlear electrode 502, may allow for a "normalized" evoked response to be recorded while electrode array 114 is inserted during surgery. In other words, a surgeon may know that changes in evoked responses recorded with extra-cochlear electrode 502 are due to real changes in the source of the evoked responses as opposed to being due to changes in the relative position of electrode array 114 with respect to the source of the evoked responses.

In cases where the extra-cochlear electrode 502 is a stapedius electrode, programming device 120 may use the stapedius electrode to record a stapedius response associated with the stapedius muscle. As used herein, a "stapedius response" refers to an evoked response generated when the stapedial muscle contracts in response to stimulation (e.g., electrical stimulation at or above a most comfortable level ("M level") associated with the patient). Programming device 120 may set a maximum power output ("MPO") for the acoustic stimulation based on the stapedius response and/or perform any other action in accordance with the stapedius response as may serve a particular implementation.

Various predetermined actions that may be performed by programming device 120 in accordance with an evoked response (or in accordance with a lack of an occurrence of an evoked response) will now be described. It will be recognized that the predetermined actions described herein are merely illustrative of the many different types of predetermined actions that may be performed in accordance with an evoked response.

In some examples, programming device 120 may set (e.g., adjust) one or more control parameters governing operation of cochlear implant system 104 in accordance with an evoked response that occurs in response to stimulation provided by cochlear implant system 104 and/or receiver 124.

Figure 6:
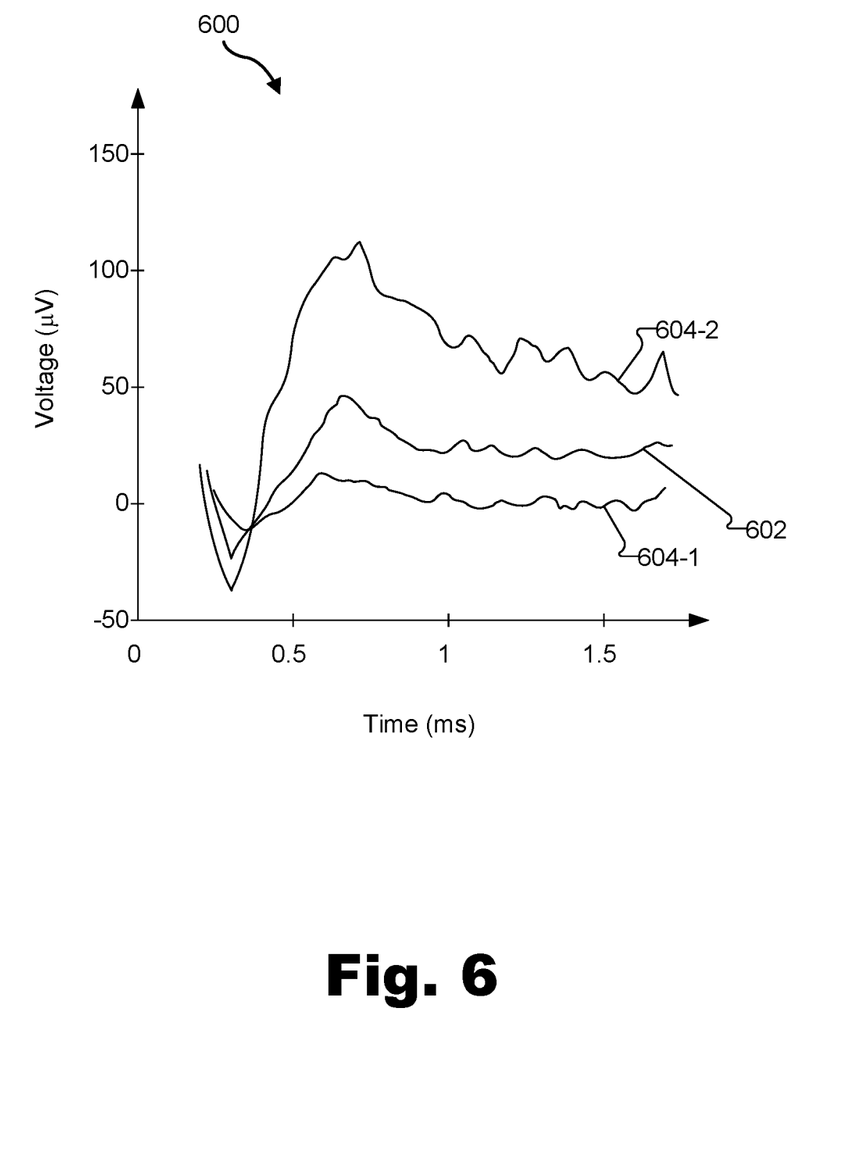
FIG. 6 shows an exemplary baseline response and two possible evoked responses according to principles described herein.

For example, programming device 120 may record an evoked response that occurs in response to electrical and/or acoustic stimulation and compare the evoked response to a baseline response and/or one or more previously recorded evoked responses. As used herein, a "baseline response" refers to some type of fixed evoked response that a clinician may consider to be normal, acceptable, and/or desirable. To illustrate, FIG. 6 shows an exemplary baseline response 602 and two possible evoked responses 604-1 and 604-2 that may occur in response to stimulation provided by cochlear implant system 104 and/or receiver 124. As shown, evoked response 604-1 is less than baseline response 602 (i.e., evoked response 604-1 has a steady state amplitude that is less than a steady state amplitude of baseline response 602). Conversely, evoked response 604-2 is greater than baseline response 602 (i.e., evoked response 604-2 has a steady state amplitude that is greater than a steady state amplitude of baseline response 602).

If the evoked response (e.g., evoked response 604-1) differs from the baseline response (e.g., baseline response 604-2) and/or the one or more previously recorded evoked responses (e.g., if the evoked response is not within a predetermined range of the baseline response and/or the one or more previously recorded evoked responses), programming device 120 may adjust one or more control parameters governing an operation of cochlear implant system 104 (e.g., by increasing an amplitude and/or intensity level of the stimulation provided by cochlear implant system 104 and/or adjusting one or more other characteristics of the stimulation).

Programming device 120 may additionally or alternatively provide one or more notifications to the patient and/or another user in accordance with an evoked response that occurs in response to stimulation provided by cochlear implant system 104 and/or receiver 124.

For example, if an evoked response is not within a predetermined range of a baseline response and/or one or more previously recorded evoked responses, programming device 120 may provide the patient and/or another user with a notification. The notification may be an audible alert (e.g., one or more beeps), a visible alert (e.g., a flashing of an LED), a text-based alert, and/or any other type of notification as may serve a particular implementation. The patient and/or other user may then take appropriate action.

Programming device 120 may additionally or alternatively evaluate a residual hearing status of the patient in accordance with an evoked response that occurs in response to stimulation provided by cochlear implant system 104 and/or receiver 124. A variety of different factors may affect a residual hearing status of a patient. For example, wax buildup in the ear, infection, sickness, patient age, and/or any other factor may temporarily and/or permanently affect a residual hearing status of the patient.

To evaluate the residual hearing status of the patient, programming device 120 may direct receiver 124 to apply acoustic stimulation to the patient. Programming device 120 may then determine whether an evoked response occurs in response to the acoustic stimulation. If an evoked response does not occur, programming device 120 may notify the clinician accordingly (e.g., by presenting a notification by way of a display device) and/or automatically determine that the patient does not have any residual hearing.

Conversely, if an evoked response does occur in response to the acoustic stimulation, programming device 120 may analyze one or more characteristics of the evoked response and, based on the analysis, determine that the patient is a candidate for an EAS system. For example, if both a cochlear response and a neural response occur in response to the acoustic stimulation, programming device 120 may determine that the patient is a candidate for an EAS system. In some examples, programming device 120 may provide a notification (e.g., by way of a display screen) that the patient is a candidate for an EAS system.

Programming device 120 may additionally or alternatively evaluate the residual hearing status of the patient by comparing the evoked response to a previously recorded evoked response and determine, based on a comparison, that the patient's residual hearing is changing (e.g., deteriorating). In response, programming device 120 may notify the patient and/or another user, automatically adjust one or more control parameters governing an operation of cochlear implant system 104 (e.g., by increasing an amplitude of stimulation being provided to the user), and/or take any other action as may serve a particular implementation.

In some examples, based on the residual hearing status as determined by programming device 120, a clinician or other user may decide to provide further treatment to the patient. For example, the clinician may decide to apply systemic steroids if a drop in residual hearing is detected.

In some examples, programming device 120 may evaluate the residual hearing status by using the evoked response to measure a two-tone interaction phenomenon that occurs within the patient. When two or more tones are simultaneously presented to the cochlea, tones not originally contained in the stimulus can be generated due to active non-linear processes in the cochlea. These measurable back-propagated responses are called distortion products and are considered to be indicative of healthy cochlear activity. They can be recorded acoustically from a patient's ear canal (e.g., otoacoustic emissions) or as electrical potentials from the neurons of the auditory pathway. Two-tone inhibition (i.e., a decrease in response to one tone in the presence of the second tone) is another phenomenon that occurs in part, due to cochlear non-linearity and can be measured using evoked responses.

Programming device 120 may additionally or alternatively use the evoked response to determine one or more optimal crossover frequencies associated with the patient. As used herein, a "crossover frequency" refers to a boundary frequency that separates frequencies represented to the patient by acoustic stimulation and frequencies represented to the patient by electrical stimulation. For example, programming device 120 may first determine that the patient is a candidate for an EAS system. Programming device 120 may then determine a crossover frequency to be used by the EAS system by determining that acoustic stimulation evokes robust hair cell and neural responses until 450 Hz and designating this frequency as the crossover frequency (i.e., the apical-most electrode can start providing electrical stimulation around that frequency).

Programming device 120 may additionally or alternatively use the evoked response to detect ectopic stimulation within the patient. As used herein, "ectopic" stimulation refers to abnormal stimulation that cochlear implant system 104 may be providing to the patient. Ectopic stimulation may be indicated by equal masking on both sides of an electrode without reduction on one side. An evoked response may be indicative of ectopic stimulation in any suitable manner. For example, an irregular evoked response may be indicative of ectopic stimulation.

Programming device 120 may additionally or alternatively use the evoked response to monitor for possible nerve regeneration within the patient. Nerve regeneration may cause changes in evoked responses over time (e.g., the amplitude of evoked responses may gradually increase over time). Hence, if programming device 120 detects a gradual increase in amplitude of evoked responses over time, this may be indicative of nerve regeneration. In some examples, programming device 120 may notify the patient and/or another user of the gradual increase and/or of the possible nerve regeneration, adjust one or more stimulation parameters accordingly, and/or take any other action based on the gradual increase as may serve a particular implementation.

Programming device 120 may additionally or alternatively use the evoked response to assess (e.g., detect, characterize, etc.) tinnitus of cochlear origin in the patient. This may be performed in any suitable manner.

Programming device 120 may additionally or alternatively use the evoked response to assist in placement of electrode array 114 during an implantation procedure (i.e., surgery). For example, programming device 120 may record the evoked response during an implantation procedure in which electrode array 114 is inserted into the patient and determining, based on the evoked response, that the electrode array should be repositioned within the patient. For example, the evoked response may be abnormally low in amplitude. This may indicate that the electrode array 114 is not properly positioned within the cochlea. Programming device 120 may provide a notification of this to the surgeon, who may adjust a positioning of electrode array 114 accordingly.

Programming device 120 may additionally or alternatively determine a source (e.g., a location within the cochlea) of one or more evoked responses. This may facilitate identification of one or more regions of properly functioning hair cells, identification of one or more acoustic dead regions for purposes of determining crossover frequencies, and/or determination of whether the patient is a good candidate for electro-acoustic stimulation.

To illustrate, programming device 120 may direct receiver 124 to apply a constant level acoustic stimulus to the patient. While the acoustic stimulus is being applied, programming device 120 may use multiple electrodes 116 included in electrode array 114 to monitor for and record evoked responses (e.g., cochlear responses) that occur in response to the acoustic stimulus. Programming device 120 may then differentially compare the evoked responses and determine which evoked response has the greatest amplitude. In some examples, the electrode that records the evoked response that has the greatest amplitude corresponds to a region within the cochlea that is the source of the evoked responses.

Figure 7:
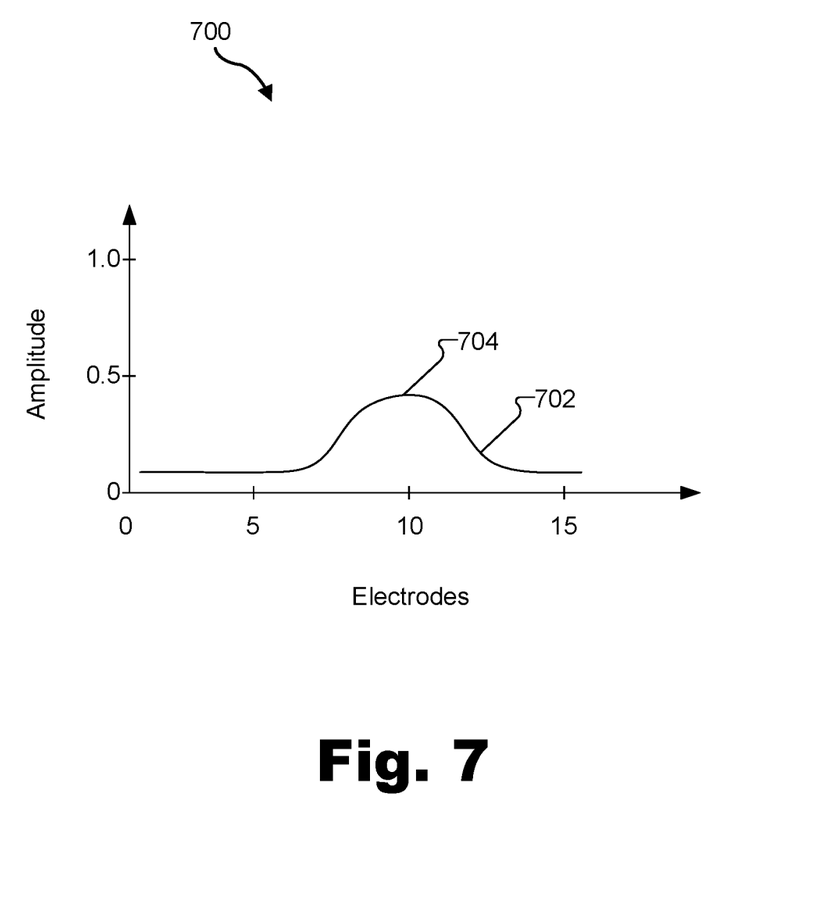
FIG. 7 shows an exemplary graph that may be presented by a programming device according to principles described herein.

In some examples, programming device 120 may present a graph of the amplitudes of the evoked responses across the different electrodes (i.e., an evoked response map) to facilitate identification by a clinician or other user of the source of the evoked responses. For example, FIG. 7 shows an exemplary graph 700 that may be presented by programming device 120 by way of a display screen associated with programming device 120. As shown, graph 700 includes an evoked response map 702 that plots the amplitude of the evoked responses measured by a plurality of electrodes. In the particular example of FIG. 7, evoked response map 702 includes a peak 704 centered at electrode 10. By viewing graph 700, a clinician may readily ascertain that the source of the evoked responses is a location within the cochlea that corresponds to the position of electrode 10 (e.g., a location associated with a frequency of approximately 750 Hz).

Additionally or alternatively, programming device 120 may automatically determine the source of the evoked responses (e.g., by identifying a maximum value included in an evoked response map similar to evoked response map 702). Programming device 120 may then take any appropriate action based on this determination (e.g., notify the clinician or another user, adjust one or more control parameters associated with cochlear implant system 104, ascertain whether the user is a candidate for an EAS system, etc.).

In some examples, programming device 120 may determine that an evoked response does not occur in response to stimulation provided by cochlear implant system 104 and/or receiver 124. Programming device 120 may accordingly notify the patient, adjust one or more stimulation parameters, and/or perform one or more other actions as may serve a particular implementation.

For example, programming device 120 may determine that a compound action potential does not occur in response to stimulation provided by cochlear implant system 104 and/or receiver 124. This may be indicative of auditory neuropathy, and may affect how cochlear implant system 104 is to be fitted to the patient. In response, programming device 120 may adjust one or more parameters of the electrical stimulation provided by cochlear implant system 104 and/or perform any other suitable action.

Programming device 120 may perform any other type of predetermined action in accordance with an evoked response as may serve a particular implementation. For example, programming device 120 may present a graph representative of the evoked response by way of a display screen, provide one or more recommendations in accordance with the evoked response (e.g., one or more recommendations with respect to setting one or more stimulation parameters that govern cochlear implant system 104), and/or perform any other suitable action as may serve a particular implementation.

In some examples, programming device 120 may perform one or more predetermined actions in accordance with a plurality of evoked responses recorded over a period of time. For example, the plurality of evoked responses, taken as a whole, may be indicative of a change in a residual hearing status of the patient. Programming device 120 may accordingly adjust one or more stimulation parameters and/or take any other suitable predetermined action as may serve a particular implementation.

Figure 8:
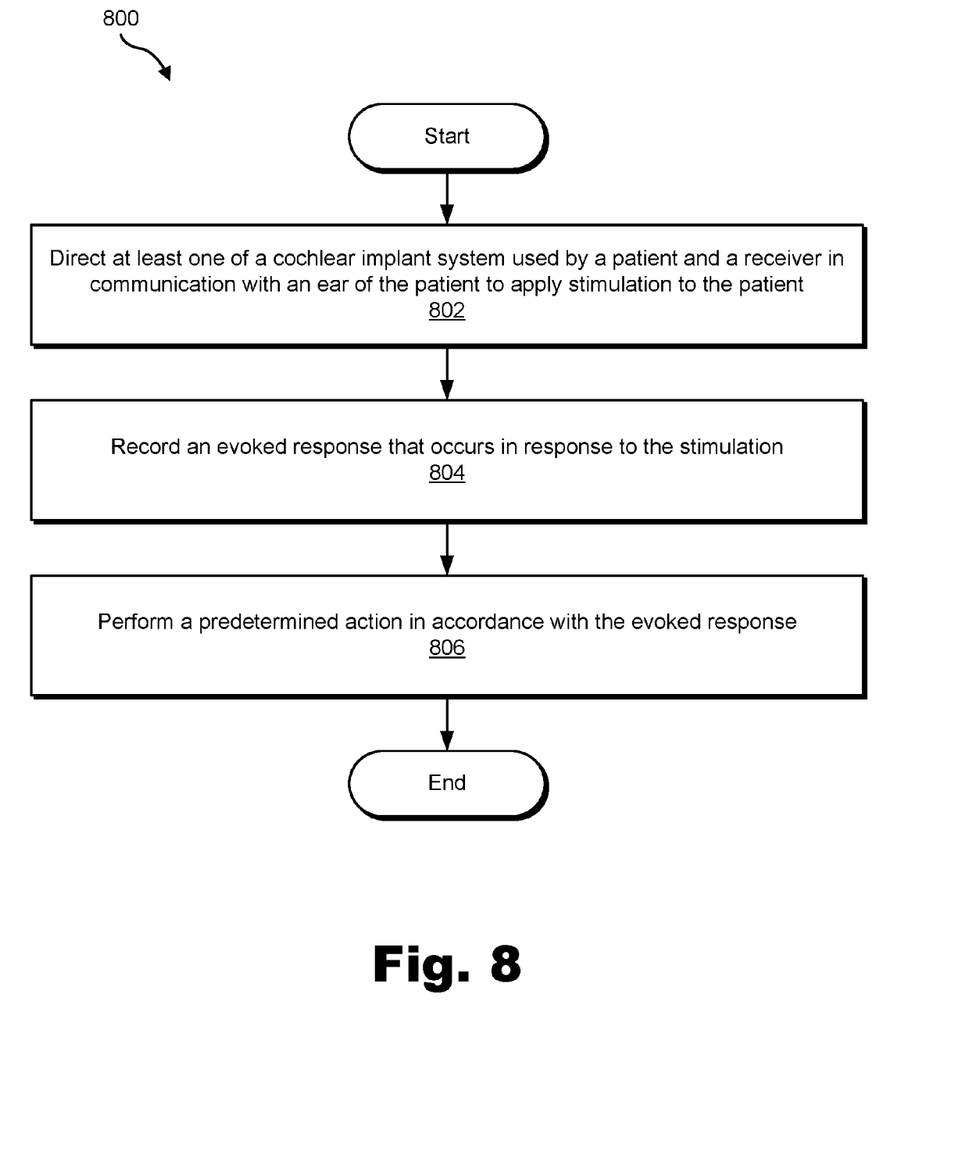
FIG. 8 illustrates an exemplary method according to principles described herein.

FIG. 8 illustrates an exemplary method 800. While FIG. 8 illustrates exemplary steps according to one embodiment, other embodiments may omit, add to, reorder, and/or modify any of the steps shown in FIG. 8. One or more of the steps shown in FIG. 8 may be performed by programming system 102 and/or any implementation thereof (e.g., programming device 120).

In step 802, a programming system directs at least one of a cochlear implant system used by a patient and a receiver in communication with an ear of the patient to apply stimulation to the patient. Step 802 may be performed in any of the ways described herein.

In step 804, the programming system records an evoked response that occurs in response to the stimulation. Step 804 may be performed in any of the ways described herein.

In step 806, the programming system performs a predetermined action in accordance with the evoked response. Step 806 may be performed in any of the ways described herein.

In certain embodiments, one or more of the processes described herein may be implemented at least in part as instructions embodied in a non-transitory computer-readable medium and executable by one or more computing devices. In general, a processor (e.g., a microprocessor) receives instructions, from a non-transitory computer-readable medium, (e.g., a memory, etc.), and executes those instructions, thereby performing one or more processes, including one or more of the processes described herein. Such instructions may be stored and/or transmitted using any of a variety of known computer-readable media.

A computer-readable medium (also referred to as a processor-readable medium) includes any non-transitory medium that participates in providing data (e.g., instructions) that may be read by a computer (e.g., by a processor of a computer). Such a medium may take many forms, including, but not limited to, non-volatile media, and/or volatile media. Non-volatile media may include, for example, optical or magnetic disks and other persistent memory. Volatile media may include, for example, dynamic random access memory ("DRAM"), which typically constitutes a main memory. Common forms of computer-readable media include, for example, a disk, hard disk, magnetic tape, any other magnetic medium, a CD-ROM, DVD, any other optical medium, a RAM, a PROM, an EPROM, a FLASH-EEPROM, any other memory chip or cartridge, or any other tangible medium from which a computer can read.

Figure 9:
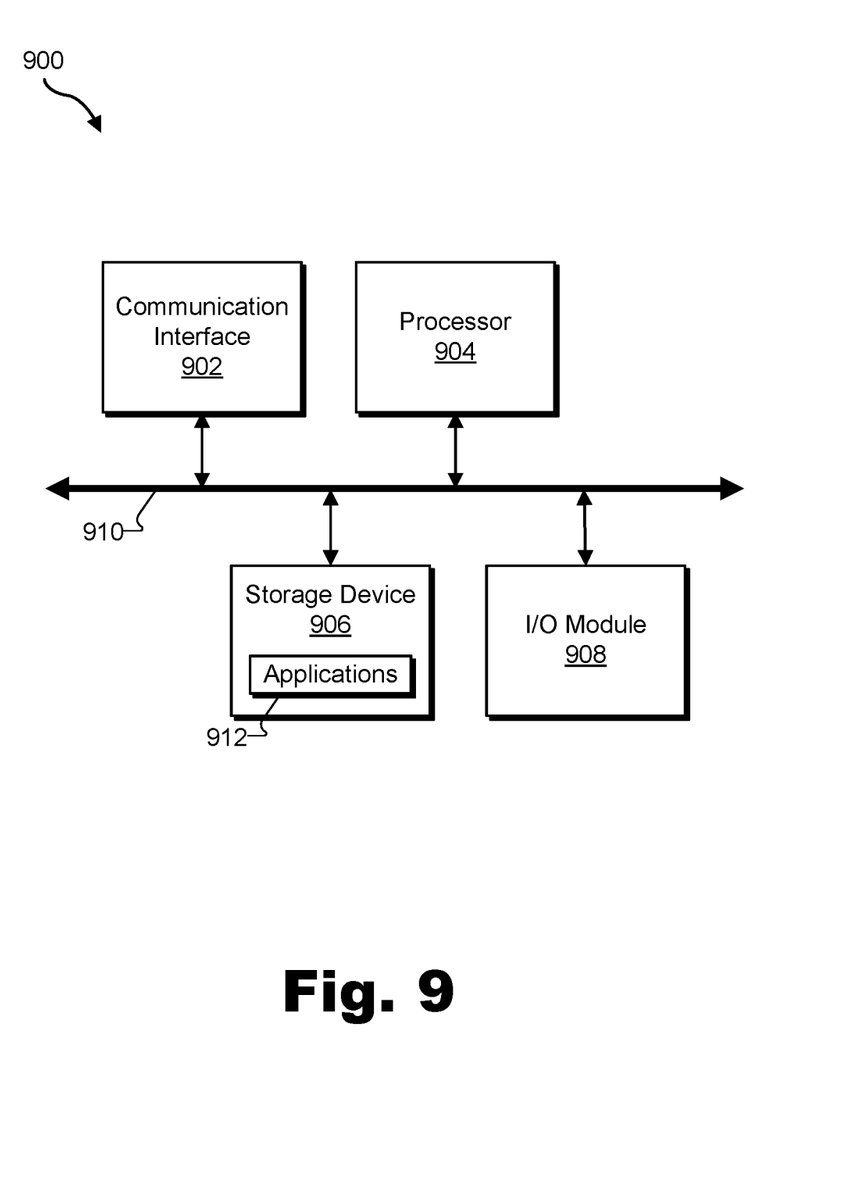
FIG. 9 illustrates an exemplary computing device according to principles described herein.

FIG. 9 illustrates an exemplary computing device 900 that may be configured to perform one or more of the processes described herein. As shown in FIG. 9, computing device 900 may include a communication interface 902, a processor 904, a storage device 906, and an input/output ("I/O") module 908 communicatively connected via a communication infrastructure 910. While an exemplary computing device 900 is shown in FIG. 9, the components illustrated in FIG. 9 are not intended to be limiting. Additional or alternative components may be used in other embodiments. Components of computing device 900 shown in FIG. 9 will now be described in additional detail.

Communication interface 902 may be configured to communicate with one or more computing devices. Examples of communication interface 902 include, without limitation, a wired network interface (such as a network interface card), a wireless network interface (such as a wireless network interface card), a modem, an audio/video connection, and any other suitable interface.

Processor 904 generally represents any type or form of processing unit capable of processing data or interpreting, executing, and/or directing execution of one or more of the instructions, processes, and/or operations described herein. Processor 904 may direct execution of operations in accordance with one or more applications 912 or other computer-executable instructions such as may be stored in storage device 906 or another computer-readable medium.

Storage device 906 may include one or more data storage media, devices, or configurations and may employ any type, form, and combination of data storage media and/or device. For example, storage device 906 may include, but is not limited to, a hard drive, network drive, flash drive, magnetic disc, optical disc, random access memory ("RAM"), dynamic RAM ("DRAM"), other non-volatile and/or volatile data storage units, or a combination or sub-combination thereof. Electronic data, including data described herein, may be temporarily and/or permanently stored in storage device 906. For example, data representative of one or more executable applications 912 configured to direct processor 904 to perform any of the operations described herein may be stored within storage device 906. In some examples, data may be arranged in one or more databases residing within storage device 906.

I/O module 908 may be configured to receive user input and provide user output and may include any hardware, firmware, software, or combination thereof supportive of input and output capabilities. For example, I/O module 908 may include hardware and/or software for capturing user input, including, but not limited to, a keyboard or keypad, a touch screen component (e.g., touch screen display), a receiver (e.g., an RF or infrared receiver), and/or one or more input buttons.

I/O module 908 may include one or more devices for presenting output to a user, including, but not limited to, a graphics engine, a display (e.g., a display screen, one or more output drivers (e.g., display drivers), one or more audio speakers, and one or more audio drivers. In certain embodiments, I/O module 908 is configured to provide graphical data to a display for presentation to a user. The graphical data may be representative of one or more graphical user interfaces and/or any other graphical content as may serve a particular implementation.

In some examples, any of the facilities and/or systems described herein may be implemented by or within one or more components of computing device 900. For example, one or more applications 912 residing within storage device 906 may be configured to direct processor 904 to perform one or more processes or functions associated with any of the facilities and/or systems described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
a programming device configured to be located external to a patient and communicatively coupled to a cochlear implant system associated with the patient, the cochlear implant system comprising a sound processor configured to located external to the patient, a cochlear implant configured to be implanted within the patient, and an electrode array configured to be located within the patient;

a programming interface device communicatively coupled to the programming device and configured to be located external to the patient; and a receiver communicatively coupled directly to the programming interface device;

wherein the programming device directs, during a period of time after an implantation procedure in which the electrode array is inserted into the patient, at least one of the cochlear implant system and the receiver to apply stimulation to the patient, records an evoked response that occurs in response to the stimulation, compares the evoked response to an additional evoked response previously recorded by the programming device during the period of time, determines, based on the comparison, that a residual hearing status of the patient has deteriorated during the period of time, increases, in response to the determination that the residual hearing status of the patient has deteriorated during the period of time, an intensity level of additional stimulation provided by the cochlear implant system in order to present audio content to the patient subsequent to the period of time, determines that the residual hearing status of the patient improves subsequent to the period of time, and decreases, in response to the determination that the residual hearing status of the patient improves subsequent to the period of time, the intensity level of the additional stimulation provided by the cochlear implant system.

2. The system of claim 1, wherein the stimulation comprises electrical stimulation, and wherein the programming device directs the cochlear implant system to apply the electrical stimulation to the patient by way of at least one electrode included in the electrode array.

3. The system of claim 1, wherein the stimulation comprises acoustic stimulation, and wherein the programming device directs the receiver to apply the acoustic stimulation to the patient.

4. The system of claim 1, wherein the stimulation comprises electrical stimulation and acoustic stimulation, and wherein the programming device concurrently directs the cochlear implant system to apply the electrical stimulation to the patient by way of at least one electrode included in the electrode array and the receiver to apply the acoustic stimulation to the patient.

5. The system of claim 1, wherein the programming device records the evoked response using an electrode included in the electrode array.

6. The system of claim 1, further comprising an extra-cochlear electrode communicatively coupled to at least one of the programming interface device and the cochlear implant system, wherein the programming device records the evoked response using the extra-cochlear electrode.

7. The system of claim 1, further comprising:
a microphone communicatively coupled directly to the programming interface device and configured to be located in an ear canal of the patient;
wherein
the evoked response comprises one or more otoacoustic emissions, and
the programming device records the one or more otoacoustic emissions using the microphone configured to be located in the ear canal of the patient.

8. The system of claim 7, wherein the programming device presents a graph representative of the evoked response by way of a display screen associated with the programming device.

9. The system of claim 1, wherein the programming device:
compares the evoked response to a baseline response; and
provides at least one of the patient and another user with a notification if the evoked response is not within a predetermined range of the baseline response.

10. The system of claim 1, wherein the programming device determines a source of the evoked response.

11. The system of claim 1, wherein the programming device:
records an additional evoked response during the implantation procedure in which the electrode array is inserted into the patient; and
determines, based on the additional evoked response, that the electrode array should be repositioned within the patient.

12. The system of claim 1, wherein the programming device uses the evoked response to determine whether the patient is a candidate for an electro-acoustic stimulation system.

13. The system of claim 1, wherein the programming device notifies at least one of the patient and another user that the residual hearing status of the patient has deteriorated.

14. The system of claim 1, wherein the receiver is not connected directly to the sound processor.

15. A system comprising:
a programming system configured to be located external to a patient;
a cochlear implant system separate from and communicatively coupled to the programming system, the cochlear implant system comprising a sound processor configured to located external to the patient, a cochlear implant configured to be implanted within the patient, and an electrode array configured to be located within the patient; and
a receiver separate from the cochlear implant system and communicatively coupled to the programming system;
wherein the programming system
directs, during a period of time after an implantation procedure in which the electrode array is inserted into the patient, at least one of the cochlear implant system and the receiver to apply stimulation to the patient,
records an evoked response that occurs in response to the stimulation, and
compares the evoked response to an additional evoked response previously recorded by the programming device during the period of time,
determines, based on the comparison, that a residual hearing status of the patient has deteriorated during the period of time,
increases, in response to the determination that the residual hearing status of the patient has deteriorated during the period of time, an intensity level of additional stimulation provided by the cochlear implant system in order to present audio content to the patient subsequent to the period of time,
determines that the residual hearing status of the patient improves subsequent to the period of time, and
decreases, in response to the determination that the residual hearing status of the patient improves subsequent to the period of time, the intensity level of the additional stimulation provided by the cochlear implant system.

16. The system of claim 15, wherein the programming system notifies at least one of the patient and another user that the residual hearing status of the patient has deteriorated.

17. A method comprising:
directing, by a programming system, at least one of a cochlear implant system used by a patient and a receiver in communication with an ear of the patient to apply stimulation to the patient, wherein
  the cochlear implant system comprises a sound processor configured to located external to the patient, a cochlear implant configured to be implanted within the patient, and an electrode array configured to be located within the patient, and
  the directing is performed during a period of time after an implantation procedure in which the electrode array is inserted into the patient;
recording, by the programming system, an evoked response that occurs in response to the stimulation;
comparing, by the programming system, the evoked response to an additional evoked response previously recorded by the programming device during the period of time;
determining, by the programming system based on the comparison, that a residual hearing status of the patient has deteriorated during the period of time;
increasing, by the programming system in response to the determining that the residual hearing status of the patient has deteriorated during the period of time, an intensity level of additional stimulation provided by the cochlear implant system in order to present audio content to the patient subsequent to the period of time;
determining, by the programming device, that the residual hearing status of the patient improves subsequent to the period of time; and
decreasing, by the programming device in response to the determining that the residual hearing status of the patient improves subsequent to the period of time, the intensity level of the additional stimulation provided by the cochlear implant system.

18. The method of claim 17, wherein the stimulation comprises electrical stimulation, and wherein the directing of the cochlear implant system to apply the stimulation comprises directing the cochlear implant system to apply the electrical stimulation by way of at least one electrode included in the electrode array.

19. The method of claim 17, wherein the stimulation comprises acoustic stimulation, and wherein the directing of the receiver to apply the stimulation comprises directing the receiver to apply the acoustic stimulation to the patient.

20. The method of claim 17, wherein the stimulation comprises electrical stimulation and acoustic stimulation, and wherein the directing comprises concurrently directing the cochlear implant system to apply the electrical stimulation to the patient by way of at least one electrode included in the electrode array and the receiver to apply the acoustic stimulation to the patient.

* * * * *